United States Patent [19]

Svoboda

[11] E Patent Number: Re. 33,717

[45] Reissued Date of Patent: Oct. 15, 1991

[54] LIQUID ATOMIZING DEVICE AND METHOD

[76] Inventor: Steven A. Svoboda, P.O. Box 443, Soulsbyville, Calif. 95372

[21] Appl. No.: 527,957

[22] Filed: May 24, 1990

Related U.S. Patent Documents

Reissue of:

[64] Patent No.: 4,746,067
Issued: May 24, 1988
Appl. No.: 928,842
Filed: Nov. 7, 1986

[51] Int. Cl.[5] ..... A61M 11/00

[52] U.S. Cl. ..... 239/338; 239/370; 239/432; 239/498; 239/500; 128/200.18; 128/200.21

[58] Field of Search ..... 239/338, 370, 498, 524, 239/432, 500, 518; 128/200.18, 200.21

[56] References Cited

U.S. PATENT DOCUMENTS

| | | | |
|---|---|---|---|
| 1,272,274 | 7/1918 | Kinealy | 239/500 |
| 3,097,645 | 7/1963 | Lester | 239/338 |
| 3,584,792 | 6/1971 | Johnson | 239/338 |
| 3,762,409 | 10/1973 | Lester | 128/200.14 |
| 4,136,740 | 1/1979 | Groos et al. | 239/524 |
| 4,333,450 | 6/1982 | Lester | 128/200.18 |
| 4,512,341 | 4/1985 | Lester | 128/200.21 |
| 4,566,452 | 1/1986 | Farr | 239/338 |
| 4,588,129 | 5/1986 | Shanks | 239/338 |

*Primary Examiner*—Andres Kashnikow
*Assistant Examiner*—Karen B. Merritt
*Attorney, Agent, or Firm*—Shoemaker and Mattare, Ltd.

[57] ABSTRACT

A device and method for aerosolizing a liquid in a gas using a pressurized gas by creating the fog or "steam" at atmospheric pressure and room temperature. The liquid is drawn into the gas stream using a venturi pipe. The amount of entrained liquid is enhanced by directing the flow of liquid and gas against a deflector. Liquid entrainment is further enhanced by directing the flow past projections causing turbulence in the stream. The device may be operated in either a horizontal position or vertical position by providing a liquid passage to the perimeter of the liquid reservoir by means of an angled liquid conduit formed between a pair of cone members.

1 Claim, 3 Drawing Sheets

LIQUID ATOMIZING DEVICE AND METHOD

Matter enclosed in heavy brackets [ ] appears in the original patent but forms no part of this reissue specification; matter printed in italics indicates the additions made by reissue.

BACKGROUND OF THE INVENTION

This invention relates to those devices which mix a gas under pressure and a liquid so that the liquid is formed in minute droplets and is carried on the stream of gas. The invention further relates to those devices which incorporate a venturi device to draw the liquid into the gas stream.

Much of the early work in this field occurred in an attempt to construct carburetors for automobiles. One of the earliest spray-nozzle carburetors utilizing a venturi was invented by Maybach in 1893.

Another application of this type of device is the hand pump sprayer for applying many types of fluid in droplet form from perfume to paint.

Still another application is the nebulizer which is used to spray medicinal solutions. Much work has been done in this area by Victor E. Lester.

SUMMARY OF THE INVENTION

The gist of the present invention is the provision of a structure for increasing the turbulence in the gas/liquid mixture downstream from the discharge opening in the venturi tube.

A further improvement is the structure which increases the attitude angle at which the device will operate and consists of a tapered capillary conduit between the liquid reservoir and the downstream conduit opening.

A still further improvement is the structure which causes a decrease in the droplet size in the aerosol produced by the elongation of the constant diameter throat section of the venturi pipe.

The purpose of this invention is to provide a device and method for inexpensively creating an aerosol from a liquid and a gas which maximizes the liquid content of the mixture.

Another object is to provide an atomizer which will continue to operate even though the liquid container is turned on its side in a horizontal plane.

Still another object is to provide an aerosol device which produces a smaller droplet size than other comparable aerosol devices.

DESCRIPTION OF THE PREFERRED EMBODIMENT OF THE INVENTION

Figure 1:
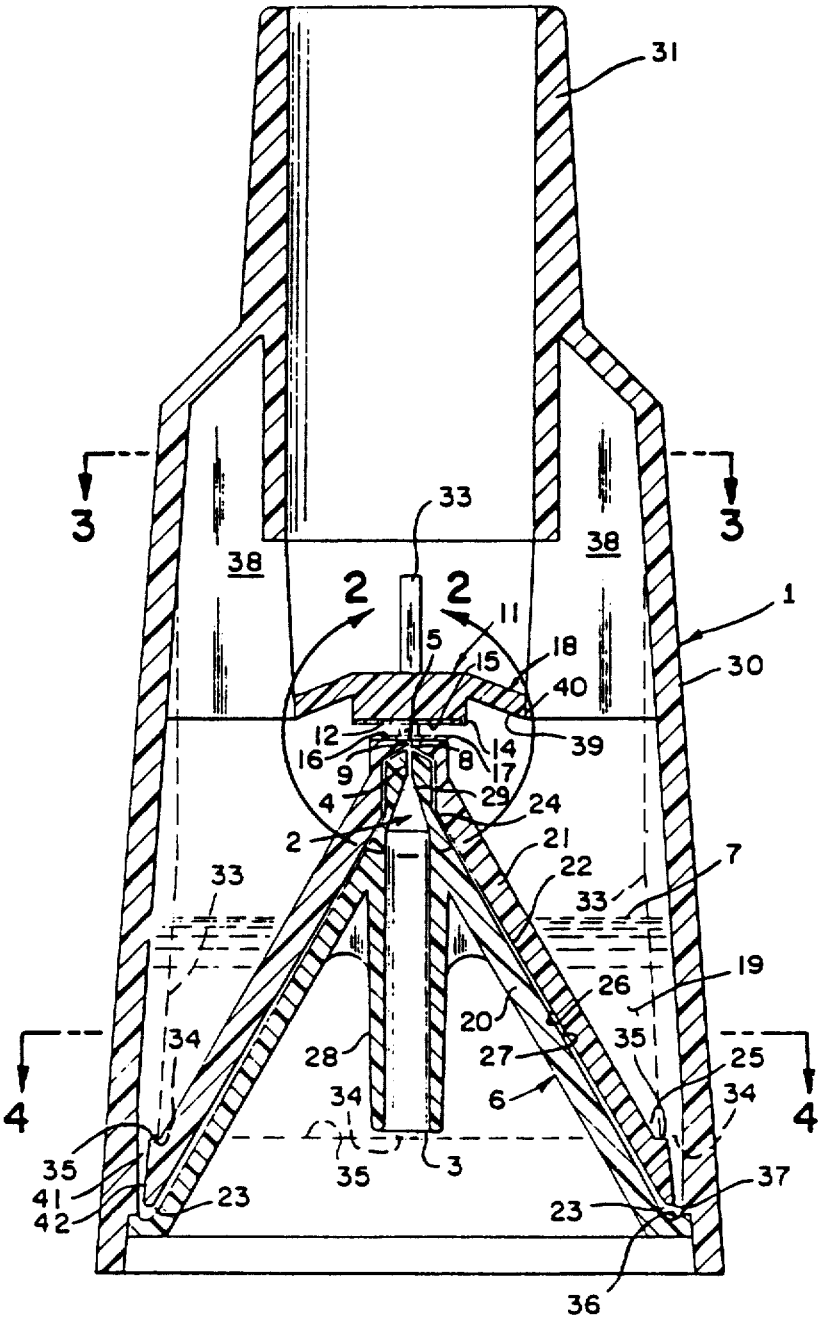
FIG. 1 is a longitudinal cross sectional view of the aerosol device of the present invention illustrating operation in a vertical position.
Figure 2:
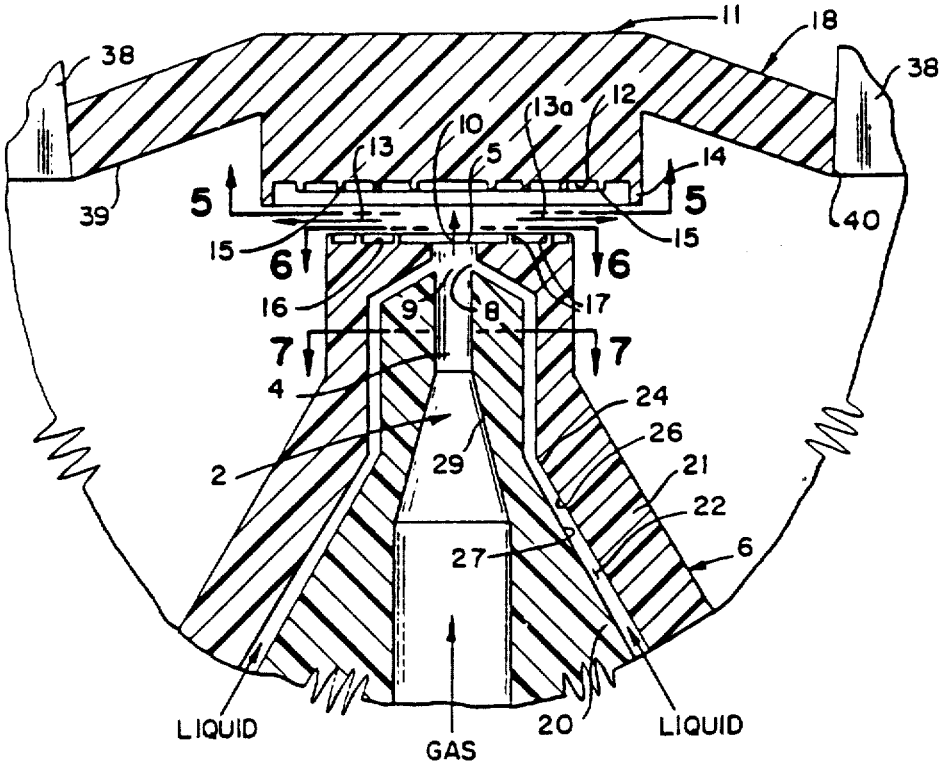
FIG. 2 is an enlarged cross sectional view of the device taken generally in the area of line 2—2 in FIG. 1.
Figure 5:
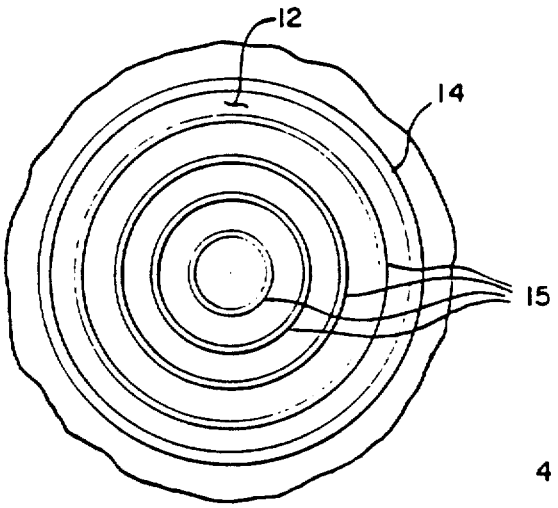
FIG. 5 is an end view of the deflector member taken along line 5—5 of FIG. 2.
Figure 6:
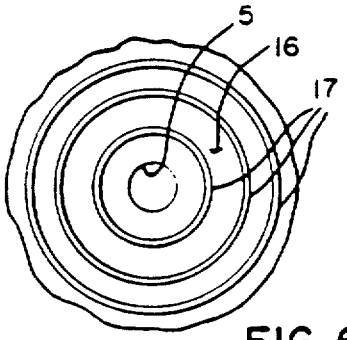
FIG. 6 is [is] an end view of the discharge surface taken along line 6—6 of FIG. 2.
Figure 7:
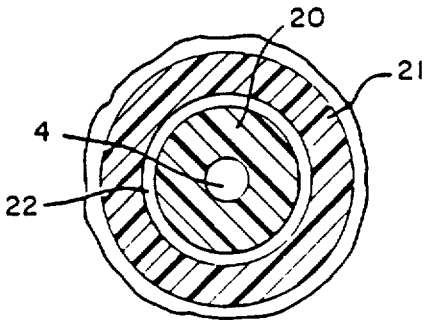
FIG. 7 is a cross sectional view taken along line 7—7 of FIG. 2.

The present invention consists of a device for aerosolizing a liquid with a gas including a container 1 for holding the liquid; a venturi tube 2 having an upstream opening 3 adapted for connection to a source of pressurized gas not shown, a throat portion 4 and a discharge opening 5; liquid conduit means 6 connected to a container 1 holding a liquid 7 and having an outlet opening 8 adjacent the downstream end 9 of the throat portion 4 of the venturi tube 2; a venturi tube 2 dimensioned and position to withdraw the liquid from the container 1 through the conduit means 6 and to project a mixture of liquid and gas out the outlet opening 5 at high velocity in a directed stream in a first direction indicated by arrow 10; a deflector member 11 positioned adjacent and disposed from the discharge opening 5 of the venturi tube 2 and having a surface 12 intersecting the directed stream which may be represented by the directional arrow 10 and causing a dispersion of the liquid and gas forming a flow mass in a second direction 13 at an angle to the first direction; and a deflector member 11 formed with a projection member 14 disposed at an angle to the deflector surface 12 and disposed at an angle from the discharge opening 5 of the venturi tube 2, causing turbulence in the flow mass; and the aforesaid structure resulting in the liquid fluid being dispersed as a fine mist in a flow of the gas fluid.

In the structure illustrated, a substantial portion of the liquid will be atomized as the liquid and gas leave the discharge opening 5 due to the pressure drop as the gas leaves the pressurized venturi tube 2 into a chamber substantially at atmospheric pressure.

The atomized stream striking the surface 12 causes further reduction in liquid droplet size and in the structure illustrated, the flow mass is turned at an approximately 90 degree angle and flows in a 360 degree flow path. Additional arrow 13a has been added to indicate this 360 degree flow path.

In a preferred form of the invention as illustrated in the drawings, the surface 12 of the deflector member 11 is a [a] generally planar surface.

In a further preferred form of the invention, the deflector member is a disc with the projection member 14 having a dimension substantially encircling the perimeter of the disc. The purpose of the projection 14 is to cause further turbulence to the flow mass to retain the liquid in the tiny droplet state and reduce the tendency of the droplets to coalesce and fall back into the liquid reservoir.

In a still further form of the invention, a plurality of concentric projection rings 15 project a lesser distance from the surface 12 of the deflector 11 than the projection member 14 and are disposed inwardly from the projection member. These concentric projection rings 15 also add to the turbulence in the flow mass.

In another form of the invention, the discharge opening is formed in a discharge surface 16 which is generally parallel with the deflector surface 12 and the discharge surface 16 is formed with a plurality of concentric ring projections 17 for creating turbulence in the flow mass.

As shown in the illustrations, a flange member 18 is connected to the deflector member and projects radially outwardly from the projection member 14 and is disposed downstream from the surface 12 of the deflector member. This flange, which may be annular in shape, prevents the unobstructed flow of gas and liquid directly out of the container.

A unique feature of the present atomizing device is the use of a unique structure to feed liquid from the liquid reservoir to the point where it joins the pressurized high velocity gas stream. All atomizers known to applicant use a conduit having a constant cross section and thus the liquid moves through the conduit at a relatively constant velocity. In contrast, the present device is furnished with a conduit which decreases in cross section as the liquid approaches the juncture with the gas stream. As previously stated, the conduit means 6 is connected to the liquid reservoir 19. Rather than consisting of a single conduit such as a small pipe, the conduit means 6 consists of a pair of cones 20 and 21 which create an opening 22 having an annular conical configuration of gradually decreasing tapered cross section.

As an example, the width of opening 22 at the inlet opening 23 is approximately 0.014" and narrows to 0.008" adjacent the apexes of the cones in the vicinity of point 24. The decrease in cross section of the liquid conduit causes the movement of the liquid to increase in velocity as the liquid moves from the reservoir to the liquid discharge opening 8.

A novel feature of the present device is that it will withdraw fluid from the reservoir and operate in every position between a vertical and horizontal attitude. This feature is made possible by providing a liquid conduit opening adjacent the entire outer perimeter of the liquid reservoir of the container. Furthermore, the lower portion of the liquid reservoir narrows to a cone configuration with the apex 25 of the cone occurring adjacent the liquid inlet opening 23. Thus, as the liquid reservoir empties, the liquid flows into the narrowing portion 25 of the reservoir 19 and thus almost all of the liquid may be withdrawn from the reservoir in all attitudes of the device between the vertical and the horizontal.

The novel structure which makes the nearly complete emptying of the reservoir possible is the construction of the conduit means with an inner and an outer cone wherein the outer cone 20 forms the bottom wall of the container and the inner cone 21 forms the inner wall of the liquid reservoir and the space 22 between the cones forms the liquid conduit 6 between the reservoir 19 and the liquid discharge opening 8.

The liquid conduit opening is formed by the inner walls 26 and 27 of the cones with the walls spaced so closely together that movement of the liquid through the liquid conduit actually occurs by capillary action. Thus a supply of liquid is applied to the pressurized air stream in the venturi up to the nearly total emptying of the reservoir.

It has been found that a substantially greater percentage of liquid is entrained in the gas using the present device. Applicant is not certain of the reason for this fact, but believes that the structure of the liquid conduit means 6 contributes substantially to this result. As shown in the illustration, the liquid conduit means 6 is positioned at a substantial angle to the longitudinal axis of the device. Thus, liquid is never required to move vertically against the force of gravity regardless whether the device is positioned vertically or horizontally.

Applicant is not able to explain the nearly complete atomization of the liquid into the gas, but it is believed that one of the contributing factors is the structure which causes a nearly laminar flow of gas to occur in the throat portion 4 of the venturi tube and then an abrupt decrease in pressure immediately followed by a violent turbulence of the mixture of liquid and gas.

As shown in the drawings, the throat portion 4 of the venturi tube is formed with a constant cross section for a distance greater than its diameter. Thus, the gas flowing in air tube 28 moves at a faster velocity as it moves through the necked down portion 29. Some turbulence takes place in the gas as the velocity increases. The throat portion 4 of the venturi tube, however has a [contant] *constant* cross section for about 0.060" in length for a diameter of 0.025". The smooth bore constant cross section is believed to return the gas to a more laminar flow. As the gas passes the liquid discharge opening 8, the reduced pressure caused by the venturi, causes liquid to be picked up in the gas stream. Immediately thereafter, the liquid and gas travel a very short distance of about 0.010" through a portion of the venturi of constant cross section of about 0.035" in diameter and length of about 0.010". As the liquid and gas exit the liquid and gas discharge opening 5, a great reduction in pressure occurs and the liquid becomes entrained in the gas stream.

The method of aerosolizing a liquid with a pressurized gas may be carried out by a number of different apparatus and here consists of the steps of directing a pressurized gas through a venturi tube 2 in a pressurized flow; directing a flow of liquid into the flow of gas adjacent the downstream throat portion 4 of the venturi tube forming a mixture of the liquid and gas in a rapidly moving stream; directing the mixture of liquid and gas in the stream through a chamber of reduced pressure; directing the mixture of liquid and gas in the stream against a surface 12 angularly related to the direction of flow of the mixture and causing a dispersion of the liquid and gas and a volumetrically increasing flow mass; directing the flow mass over a projection thereby causing a rapid increased turbulence of the flow mass; and the steps resulting in the liquid being dispersed as a fine mist carried by the flow of gas.

When used as a nebulizer, the container 1 is preferably made of plastic and the entire unit is designed to be used only once before disposal. It is essential, therefore, to construct the device as inexpensively as possible. The container 1 is constructed with an outer cylindrical tapered wall having a base diameter of about 1.400" and an upper wall about 1.125" in diameter. A tube 31 having a diameter of about 9/16" protrudes from the top of the container. The tube 31 is adapted for connection to a face mask or other type of manifold for administering the aerosolized liquid and gas to a patient.

Figure 4:
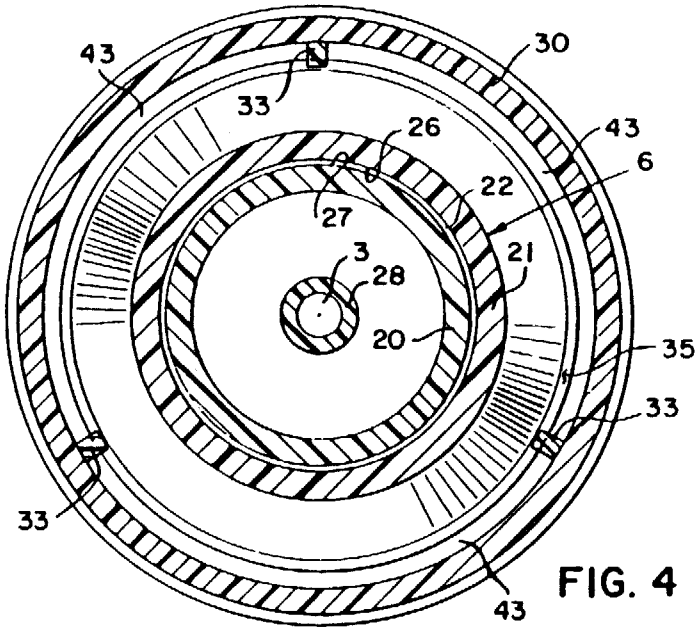
FIG. 4 is a cross-sectional view of the device taken along line 4—4 in FIG. 1.
Figure 3:
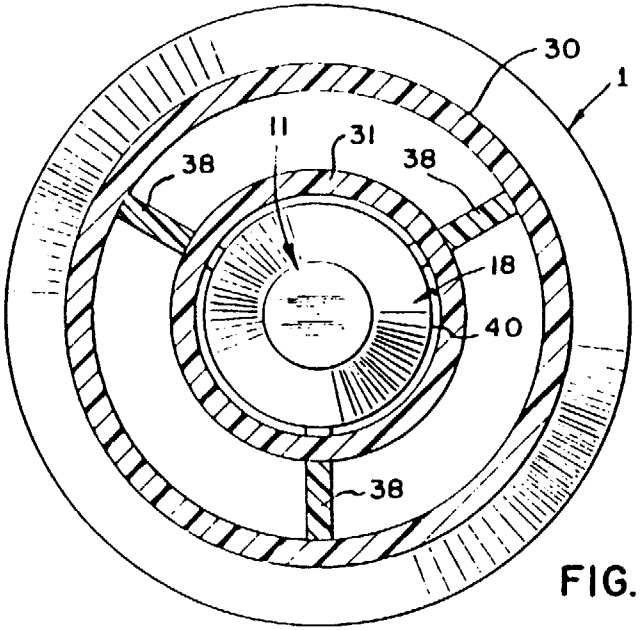
FIG. 3 is an enlarged cross sectional view of the device taken along line 3—3 in FIG. 1.
Figure 8:
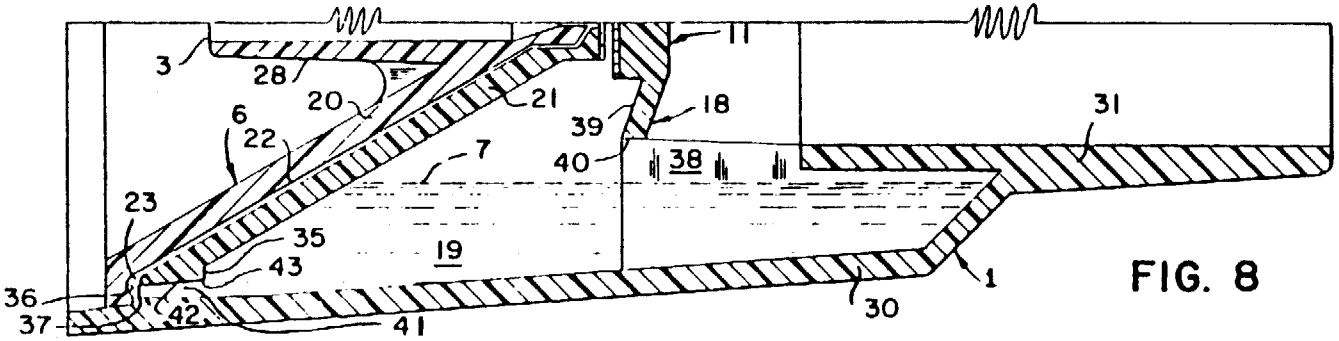
FIG. 8 is a partial cross sectional view similar to FIG. 1, but with the device shown on its side to illustrate operation on a horizontal plane.

As previously stated, the bottom wall of the container consists of a cone 20 which is attached to the outer wall 30 by any suitable method. The outer cone 20 is formed with a protruding pipe member 28 which is adapted for connection to a gas pressure source. The gas should be pressurized to about 12 to 25 psi. An inner cone 21 is spaced from the outer cone by nibs molded in one or both matching cone faces to maintain a proper spacing to form the conical liquid opening 22. The inner cone 21 is held in position by three elongated ribs 33 molded or connected to the inside of wall 30 with lower ends 34 resting on shoulders 35 formed in inner cone 21. Liquid flows from reservoir 19 to inlet opening 23 through annular openings 43 as best shown in FIG. 4. It should be noted that a radius is formed in the inside wall of outer cone 20 forming a concave depression 36 therein. A radius is also formed in the edge of inner cone 21 forming a convex edge 37. This construction reduces the space in the bottom of the container so that essentially all of the liquid can be aerosolized and provides a smooth transition between the liquid reservoir 19 and the liquid conduit means 6. Additional ribs 38 extend from the inside of wall 30 and support deflector member 11.

The deflector member is preferably circular with a diameter of about 0.500". The outer portion 39 of the disc slants downwardly preventing liquid and gas flow directly through tube 31 and creating a space downstream of projection 14 creating further turbulence of the stream of liquid and gas fog.

It has been found that capillary movement of the liquid through the liquid conduit means 26 is enhanced if the surfaces 26 and 27 of the cones have a slight texture of 16 to 200 rms. A finish of 64 rms have been found to be optimal. The textured finish may be obtained by sand blasting the mold. The texture may be further defined by the commercial name "Mold Tech 1055".

Operation of the atomizing device is as follows. Liquid is poured into the container until the level of the liquid is at any level below the gas and liquid discharge opening 5. Pipe member 28 is then attached to a source of pressurized gas by a hose or other suitable means. The gas should be pressurized to about 12 to 25 psi. The pipe member 28 is sized to give a flow of gas of about 8 liters per minute. The gas moving at high velocity through the throat portion 4 of the venturi pipe results in a reduction in pressure which picks up the liquid at annular liquid discharge opening 8. As the liquid and gas exit the liquid and gas discharge opening 5, the sudden reduction in pressure causes the liquid to be atomized and be carried in a fine mist or fog in the rapidly moving gas. This fog is sometimes referred to as "steam", but unlike steam which is caused by boiling water at high temperature, the "steam" produced by the nebulizer is at a room temperature unless the liquid in the reservoir 7 has been warmed. The rapidly moving liquid and gas strikes deflector surface 12 where it is immediately changed in direction 90 degrees to its initial direction. As the stream of fog moves over the surface 12 of the deflector, ridge projections about 0.005" in height cause turbulence in the flow. Similar projections 17 are formed in the discharge surface 16 and add to the turbulence. These projections in the discharge surface 16 may be a series of concentric ring projections about 0.005" in height.

The structure which gives the greatest degree of turbulence as the liquid and gas stream moves over the above surfaces is a projection ring 14 which depends approximately 0.015" below the surface 12 of the deflector. The stream of fog or "steam" then passes around the outer edge 40 of the deflector and passes out tube 31. The "steam" is then carried by various pipes, masks and other means to a person who breaths in the fog which may contain medicines or merely be a saline solution.

The liquid may be water or a volatile liquid for any purpose in which the liquid is to be carried in minute droplet form in an exceedingly fine vapor in a gas such as air or any other type of gas.

The present device is capable of producing up to 50% more "steam" than similar nebulizers on the market. Most of this increase in "steam" is due to the use of the projection member 14 which was discovered by accident when a molding error left a thin flashing of plastic around the deflector. Subsequent testing with the flashing left in place resulted in finding the greatly increased production of "steam".

As previously set forth, inner and outer cones were used to form the liquid conduit means. While this is the preferred form, the cones could actually be hemispherical or parabolic in shape for example.

I claim:

[1. A device for aerosolizing a liquid with a gas comprising:

a. a container for holding said liquid;

b. a venturi tube having an upstream opening adapted for connection to a source of pressurized gas, a throat portion, a gas discharge opening, and a liquid and gas discharge opening;

c. liquid conduit means connected to said container holding said liquid and having a liquid discharge opening adjacent the downstream end of said throat portion of said venturi tube;

d. said venturi tube is dimensioned and positioned to withdraw said liquid fluid from said container through said conduit means and to project a mixture of said liquid and gas out said liquid and gas discharge opening at high velocity in a directed stream in a first direction;

e. a deflector member positioned adjacent and disposed from said discharge opening of said venturi tube and having a surface formed with a generally planar surface intersecting said directed stream and causing a dispersion of said liquid and gas forming a flow mass in a second direction at an angle to said first direction; and f. said deflector member is formed with a projection member disposed at an angle to said deflector surface and disposed at an angle from said liquid and gas discharge opening of said venturi tube, causing turbulence in said flow mass;

g. said structure resulting in said liquid being dispersed as a fine mist in a flow of said gas;

h. said liquid and gas discharge opening is formed in a discharge surface which is generally parallel with said deflector surface; and i. said discharge surface is formed with a plurality of concentric ring projections for creating turbulence in said flow mass.]

*2. A device for aerosolizing a liquid with a gas comprising:*

*a. a container for holding said liquid;*

*b. a venturi tube having an upstream opening adapted for connection to a source of pressurized gas, a throat portion, a gas discharge opening, and a liquid and gas discharge opening;*

*c. liquid conduit means connected to said container holding said liquid and having a liquid discharge opening adjacent the down stream end of said throat portion of said venturi tube;*

*d. said venturi tube is dimensioned and positioned to withdraw said liquid fluid from said container through said conduit means and to project a mixture of said liquid and gas out said liquid and gas discharge opening at high velocity in a directed stream in a first direction;*

*e. a deflector member positioned adjacent and disposed from said discharge opening of said venturi tube and having a surface formed with a generally planar sur-*

*face intersecting said directed stream and causing a dispersion of said liquid and gas forming a flow mass in a second direction at an angle to said first direction; and*

*f. said deflector member is formed with a projection member disposed at an angle to said deflector surface and disposed at an angle from said liquid and gas discharge opening of said venturi tube, causing turbulence in said flow mass;*

*g. said structure resulting in said liquid being dispersed as a fine mist in a flow of said gas;*

*h. said deflector member being a disc whose perimeter is substantially encircled by said projection member and from which disc a plurality of concentric projecting rings depend, disposed inwardly from said projection member, said projecting rings projecting a lesser distance from said surface of said deflector member than said projection member.*

* * * * *